US012697485B2

(12) United States Patent
Forino

(10) Patent No.: US 12,697,485 B2
(45) Date of Patent: Aug. 4, 2026

(54) ELECTROSTIMULATION DEVICE WITH A DOUBLE PERCUTANEOUS COAXIAL NEEDLE AND PROCESS FOR MANUFACTURING THE SAME

(71) Applicant: Luciano Forino, Pianezza (IT)

(72) Inventor: Luciano Forino, Pianezza (IT)

(73) Assignee: Luciano Forino, Pianezza (IT)

( * ) Notice: Subject to any disclaimer, the term of this patent is extended or adjusted under 35 U.S.C. 154(b) by 239 days.

(21) Appl. No.: 18/719,632

(22) PCT Filed: Dec. 19, 2022

(86) PCT No.: PCT/IB2022/062488
§ 371 (c)(1),
(2) Date: Jun. 13, 2024

(87) PCT Pub. No.: WO2023/112006
PCT Pub. Date: Jun. 22, 2023

(65) Prior Publication Data
US 2025/0050097 A1      Feb. 13, 2025

(30) Foreign Application Priority Data

Dec. 17, 2021 (IT) ........................ 102021000031724

(51) Int. Cl.
*A61N 1/05* (2006.01)
(52) U.S. Cl.
CPC ................................. *A61N 1/0502* (2013.01)
(58) Field of Classification Search
None
See application file for complete search history.

(56) References Cited

U.S. PATENT DOCUMENTS

| | | | | |
|---|---|---|---|---|
| 2,923,295 A | * | 2/1960 | Guerriero | ............... A61M 5/32 |
| | | | | 604/170.01 |
| 3,078,850 A | * | 2/1963 | Schein | ................. A61N 1/3629 |
| | | | | 607/2 |

(Continued)

FOREIGN PATENT DOCUMENTS

| | | | | |
|---|---|---|---|---|
| IT | 201600089091 A1 | 3/2018 | | |
| WO | WO-2014074237 A1 | * | 5/2014 | ............. A61B 50/33 |

*Primary Examiner* — Krystal Robinson
(74) *Attorney, Agent, or Firm* — Colson Law Group, PLLC

(57) ABSTRACT

An electrostimulation device with a double percutaneous coaxial needle, comprising: two tubular bodies, in plastic material, hereinafter referred to respectively as cannula support and counter-cannula support, wherein the cannula support and the counter-cannula support are telescopically connected with the possibility of relative axial sliding; a cannula needle and a counter-cannula needle, hereinafter referred to respectively as cannula and counter-cannula, axially perforated. The cannula is supported fixed and coaxial with respect to the cannula support and the counter-cannula is supported fixed and coaxial with respect to the counter-cannula support and the counter-cannula is inserted in a coaxial arrangement and is electrically insulated with respect to the cannula, with the possibility of relative axial sliding. The cannula support is, at least partially, included within the counter-cannula support with the possibility of relative axial sliding. A process for manufacturing the electrostimulation device with a double percutaneous needle is also disclosed.

14 Claims, 9 Drawing Sheets

(56)  References Cited

U.S. PATENT DOCUMENTS

| | | | |
|---|---|---|---|
| 3,682,162 A * | 8/1972 | Colyer ................. | A61N 1/0502 604/239 |
| 5,409,453 A * | 4/1995 | Lundquist .............. | A61B 10/06 607/99 |
| 7,201,731 B1 | 4/2007 | Lundquist et al. | |
| 8,353,901 B2 * | 1/2013 | Rossetto ............ | A61B 18/1477 606/33 |
| 8,753,708 B2 * | 6/2014 | Hum ......................... | C09D 5/38 623/1.53 |
| 9,393,382 B2 * | 7/2016 | Heck ................. | A61M 25/0023 |
| 2004/0143195 A1 * | 7/2004 | Bressler ............ | A61M 25/0625 600/573 |
| 2005/0094353 A1 * | 5/2005 | Marshall .............. | A61N 1/3754 174/50.59 |
| 2017/0049507 A1 * | 2/2017 | Cosman ............. | A61B 18/1477 |
| 2019/0046791 A1 * | 2/2019 | Ebbers ................. | A61N 1/0476 |

* cited by examiner

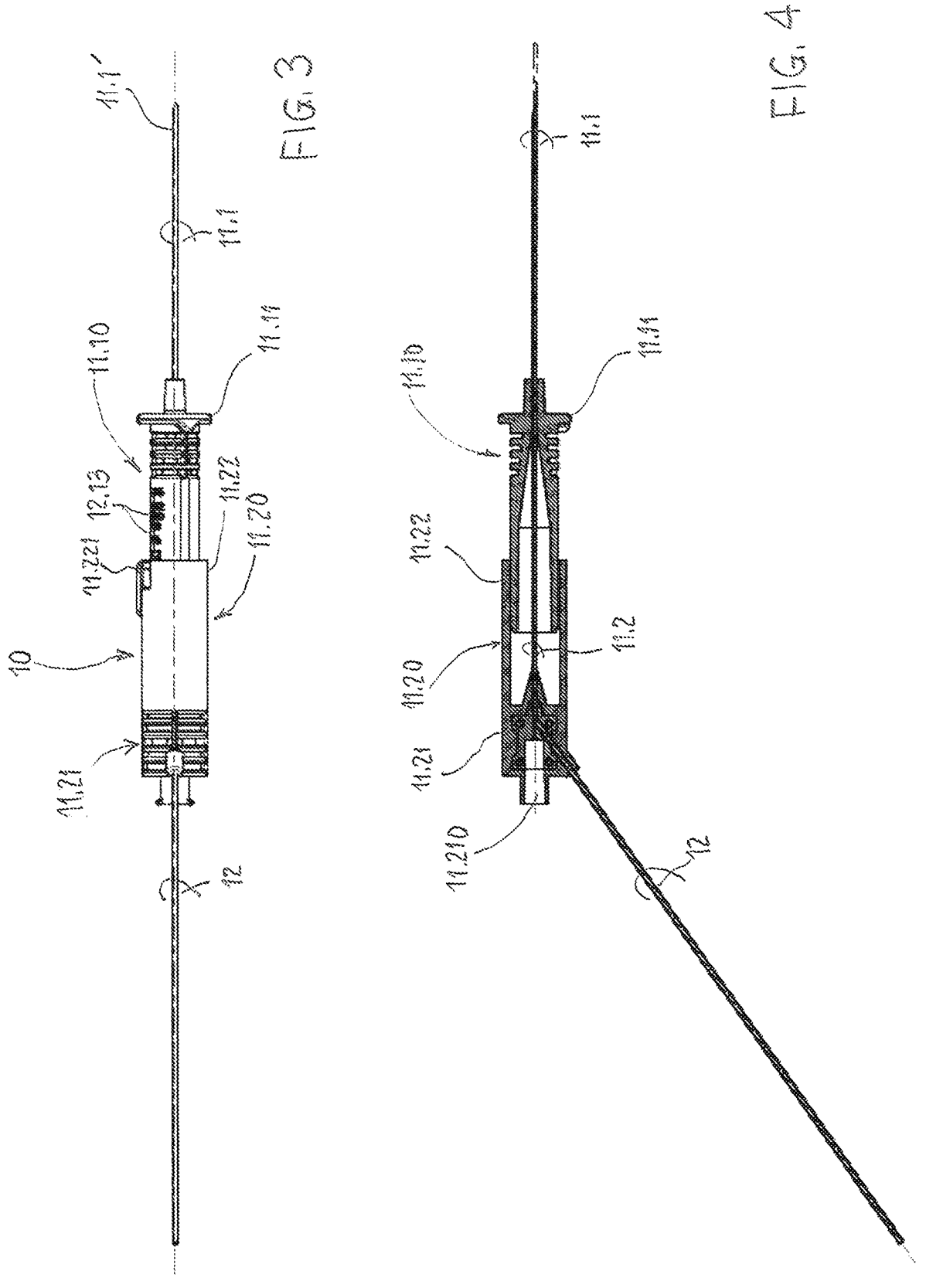

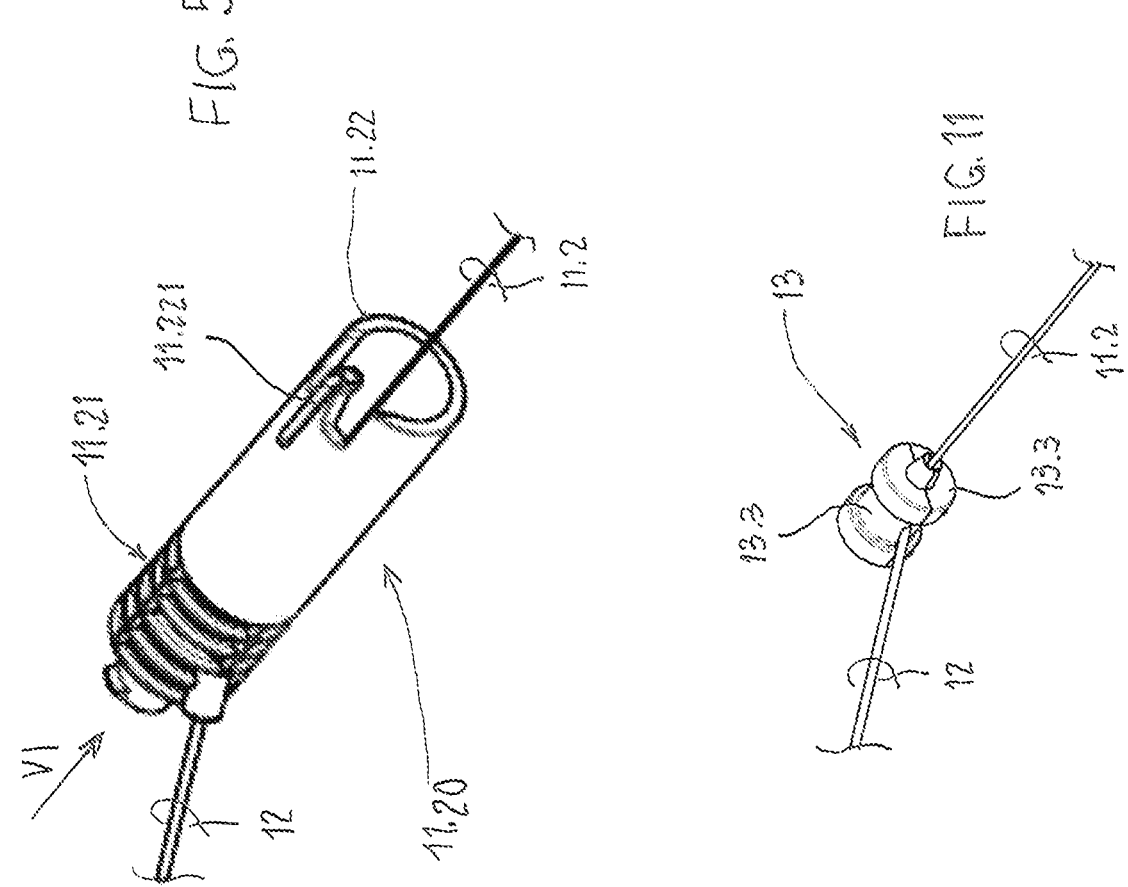

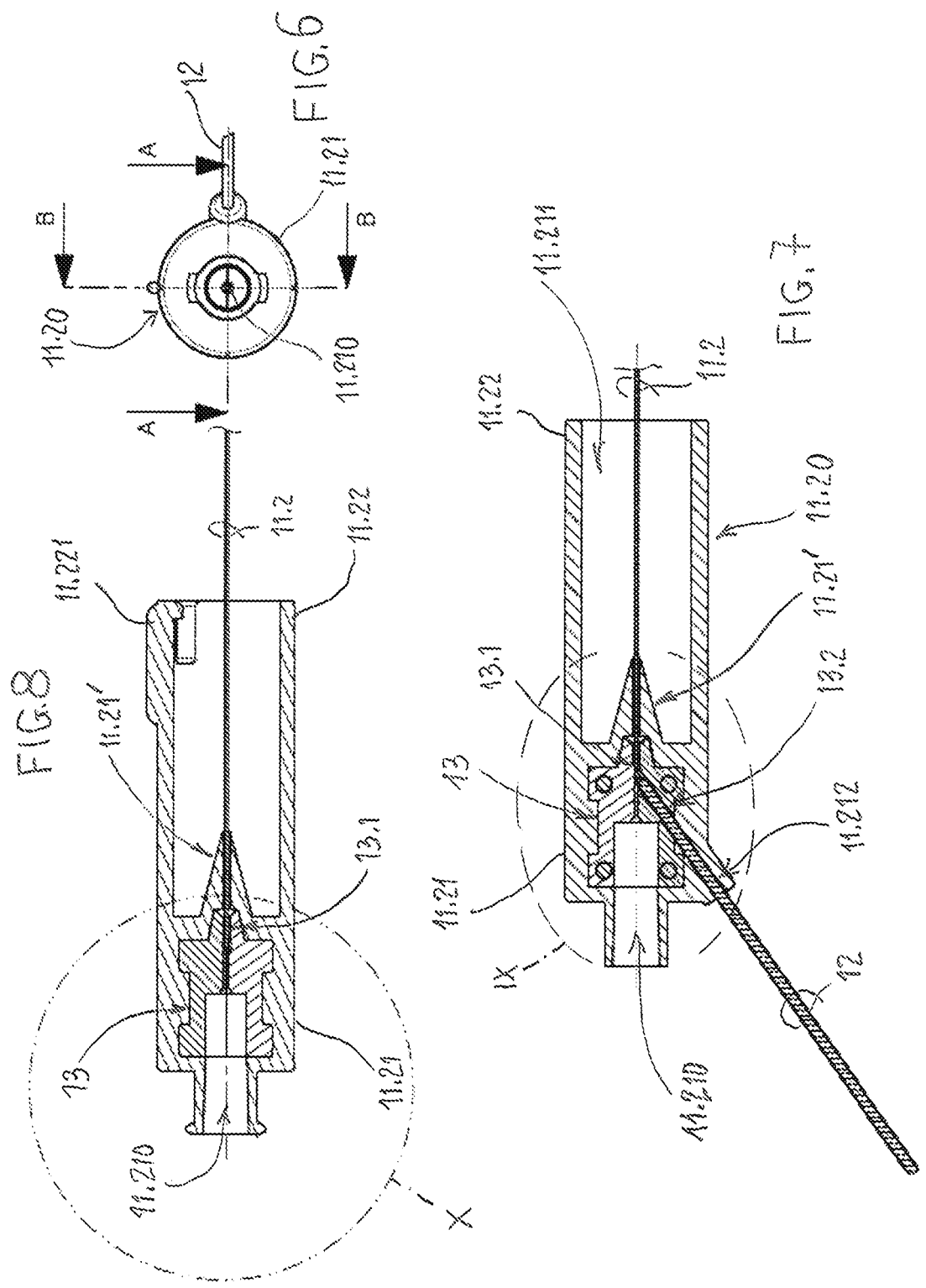

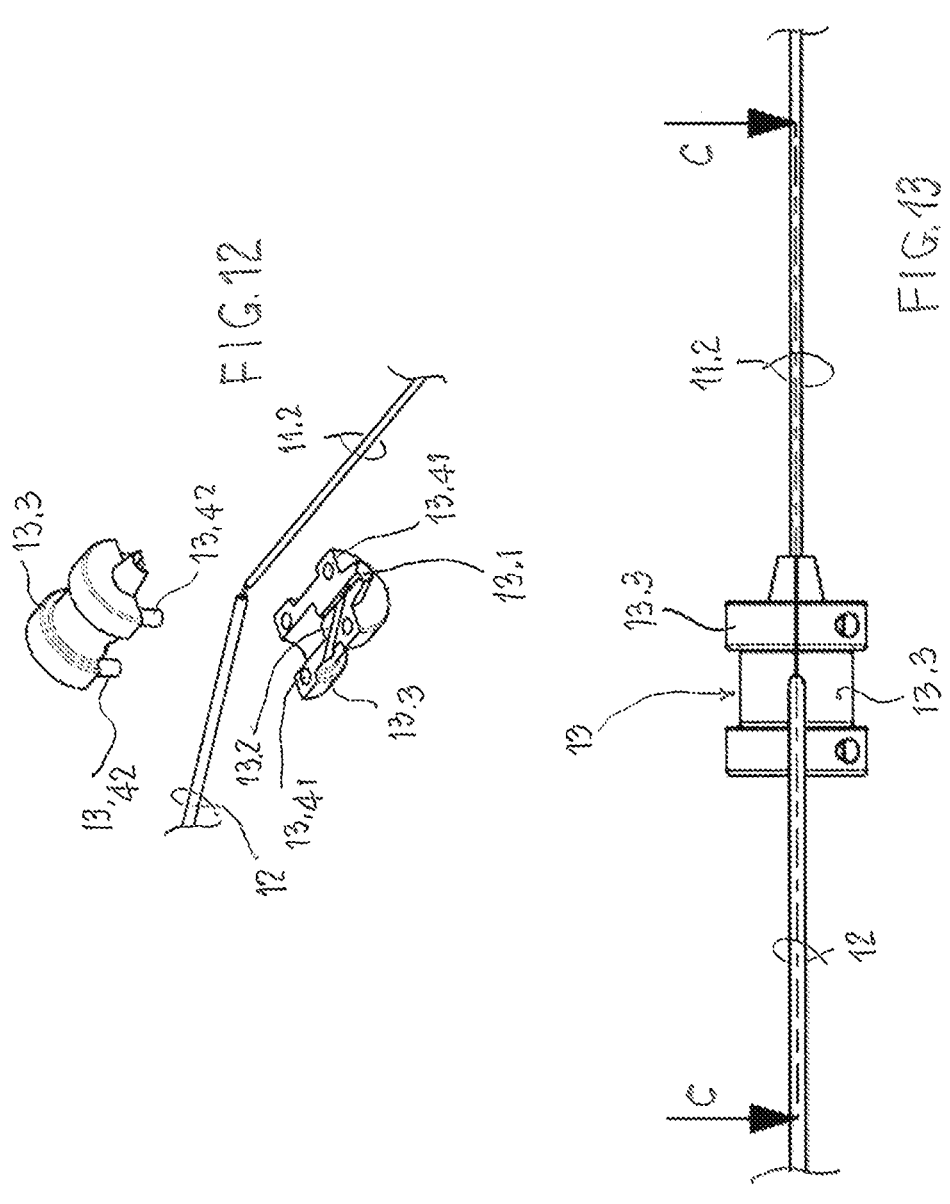

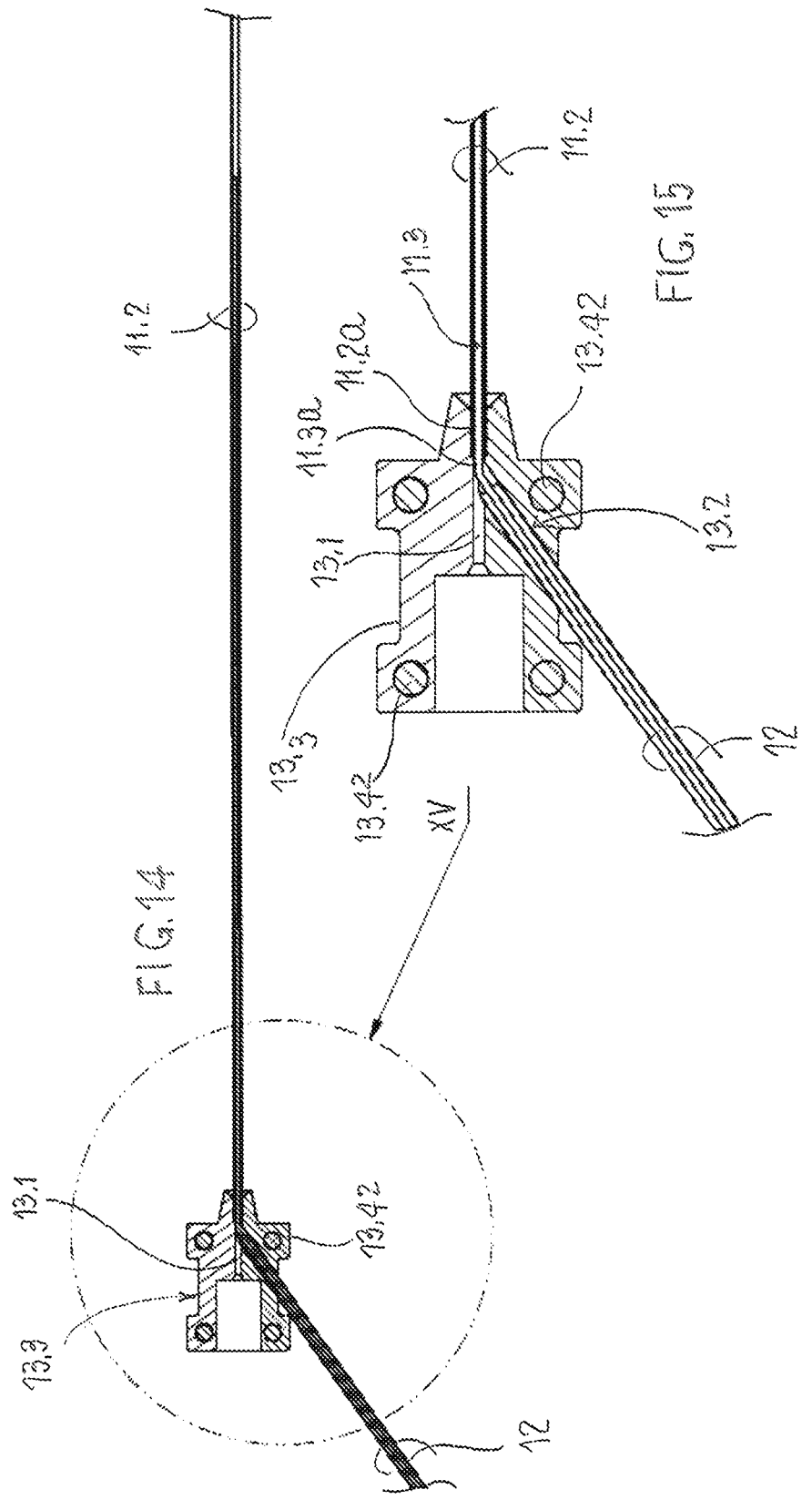

ELECTROSTIMULATION DEVICE WITH A DOUBLE PERCUTANEOUS COAXIAL NEEDLE AND PROCESS FOR MANUFACTURING THE SAME

The present invention refers to an electrostimulation device with a double percutaneous coaxial needle, in particular for minimally invasive applications of percutaneous radiofrequency in the treatment of chronic pain in hospital settings. Said electrostimulation device with double percutaneous coaxial needle will be referred to hereinafter as "device" for the sake of brevity. The invention also refers to the process for manufacturing the device specified above.

The Italian patent N. 102016000089091 of the same inventor describes a device of the specified type, in which a transcutaneous monopolar needle means that can be stimulated and thermodamaging is electrically connected in an electric circuit with respect to an electric pulse generator and to a neutral dispersion plate, so-called ground electrode, designed to close the electric circuit between a negative pole and a positive pole, for minimally invasive applications of percutaneous radiofrequency in the treatment of chronic benign pain in hospital settings.

Said needle means comprises two coaxial tubular parts, called cannula and counter-cannula respectively, wherein the cannula is external to the counter-cannula. Cannula and counter-cannula are made of electrically conductive material, for example steel, and are coupled to each other with possibility of relative axial sliding, electrically insulated and supported, at one of their ends, the so-called proximal end, by respective axially perforated and coaxial conical support bodies (in the hereinafter "support cones"), which are made of electrically insulating material, for example plastic material. The support cones are connected to each other with possibility of relative axial sliding and, in particular, the support cone of the cannula has an internal axial cavity with a conical surface and the support cone of the counter-cannula has a conical external axial surface, configured to achieve a geometric coupling with respect to the conical cavity of the cannula support cone.

Cannula and counter-cannula are provided at their other axial end, the so-called distal end, with respective tips. The cannula has a cutting tip, suitable for skin puncture only, while the counter-cannula has a non-cutting tip.

Furthermore, the cannula is completely isolated externally by an electrically and thermally insulating coating.

The counter-cannula includes a so-called U.T.A. ("Uncoring Tip Advance") type electrode probe.

The support cone of the counter-cannula comprises electrical connector means, configured for the electrical connection of the electrode probe with respect to the electrical pulse generator. An insulated electrical conductor is electrically connected with respect to said electrical connector means and extends outside the support cone of the counter-cannula, through the conical cavity of the support cone of the cannula.

Furthermore, the support cone of the cannula and the support cone of the counter-cannula comprise respective guide and reciprocal retention means, which are configured to allow successive steps of manual advancement and retraction of the counter-cannula with respect to the cannula, by means of relative axial sliding of the support cone of the counter-cannula in relation to the support cone of the cannula, maintaining the counter-cannula in a corresponding stable relative arrangement with respect to the cannula at each step. Specifically, in a first relative arrangement of the counter-cannula with respect to the cannula, the cutting tip of the cannula can perform skin penetration into a patient's body. In a second and subsequent relative arrangement of the counter-cannula with respect to the cannula, the tip of the counter-cannula protrudes at least partially with respect to the tip of the cannula and overlaps the cutting edge of the cannula itself, which is thus made no longer sharp, while the tip of the counter-cannula is arranged for the treatment. In at least a third and further relative arrangement of the counter-cannula with respect to the cannula, the counter-cannula is further advanced with respect to the tip of the cannula, and the needle means, including the cannula and the counter-cannula, is advanced into the subcutaneous planes and structures of the patient, until the operating target, without generating any type of accidental complication.

The device according to the aforementioned patent has the following drawbacks:
the guide and reciprocal retention means provided in the support of the cannula and in the support of the counter-cannula are also limited in their axial stroke by the presence of the insulated electric conductor. The support body of the cannula cannot be made to the desired length. In fact, an axial lengthening of the support body of the cannula, while it allows to increase the number of stable relative positions of the counter-cannula with respect to the cannula, also increases the risk of undesired erroneous positioning of the electrical conductor in the cavity of the support cone of the cannula with consequent possible device malfunctions. In fact, once the skin puncture has been performed, the U.T.A. electrode probe is advanced within the electrically isolated cannula. The relative bidirectional movement of the two support cones and, correspondingly, of the counter-cannula with respect to the cannula, allows the operator to achieve the desired operative arrangements of the cannula (in cutting or non-cutting condition) and, during the treatment phase, to choose which active tip to use, cannula tip or counter-cannula tip. Any jamming of the insulated electrical conductor, which is moved together with the support cone of the counter-cannula into the internal cavity of the support cone of the cannula, can hinder correct operation;
on the other hand, the insulated electric conductor occupies part of the cavity of the cannula support body, partly passes through this cavity and emerges from it in a substantially axial direction. This arrangement of the insulated electrical conductor complicates both the structure and the manufacturing process of the percutaneous coaxial needle device.

Document WO 2014/074237 A1 discloses an electrostimulation device with a double percutaneous coaxial needle having the characteristics of the pre-characterizing part of claim 1.

The present invention intends to remedy the aforementioned drawbacks of the prior art and provide a device of the type specified which allows to improve the use of the device itself and its production.

An object of the present invention is to provide an electrostimulation device with a double percutaneous coaxial needle, in particular for minimally invasive percutaneous radiofrequency applications in the treatment of chronic pain in hospitals, which allows the above applications to be performed correctly and effectively.

Another object of the present invention is to provide a device of the type specified which is improved, both functionally and structurally.

Another object of the present invention is also to provide a process for manufacturing an electrostimulation device with a double percutaneous coaxial needle of the type specified, which is easy and reliable to implement.

In view of these objects, the present invention provides an electrostimulation device with a double percutaneous coaxial needle, the essential characteristics of which form the subject-matter of claim 1.

The invention also provides a process for the manufacturing an electrostimulation device with double percutaneous coaxial needle, the essential characteristics of which form the subject of claim 8.

Other advantageous features of the present invention are described in the dependent claims.

Further features and advantages of the invention will be apparent from the following detailed description of an example of embodiment, with reference to the drawing which shows important details for the invention, and from the claims.

The features illustrated here must not necessarily be considered to scale and are represented in such a manner that the particular characteristics according to the invention are clearly highlighted.

The various features can be produced individually or in any combination with one another, as variants of the invention.

In the drawing:

FIG. 1 is a perspective view of the electrostimulation device with double percutaneous coaxial needle, in a monopolar version, according to a first exemplifying embodiment of the invention, comprising a cannula needle with relative support and a counter-cannula needle with relative support illustrated mutually connected, in which the cannula needle with relative support is interconnected and partially extended with respect to the counter-cannula needle with relative support and the device is seen from the rear;

FIG. 3 is an elevation view of the device of FIG. 1, on a different scale;

FIG. 4 is an axial sectional view of the device of FIG. 3;

FIG. 5 is a perspective view, from the front, of the counter-cannula needle of FIG. 2 (interrupted for clarity of illustration) with relative support, in different scales;

FIG. 6 is a view of the support of the counter-cannula needle in the direction of arrow VI of FIG. 5, on a different scale;

FIG. 7 is a sectional view along the line A-A of FIG. 6;

FIG. 8 is a sectional view along the line B-B of FIG. 6;

FIG. 11 is a perspective view, on a different scale, of a mounting body of the counter-cannula needle and of an electric conductor, said mounting body being included in the support of the counter-cannula needle, as illustrated for example in FIG. 9;

FIG. 12 is a view similar to that of FIG. 11, but in which said mounting body is shown in an exploded view, with relative cannula needle and electric conductor;

FIG. 13 is a side elevational view of the mounting body of the counter-cannula needle, with related cannula needle and electrical conductor, according to FIG. 11;

FIG. 14 is a sectional view along the line C-C of FIG. 13, on a different scale;

4

Figure 1:
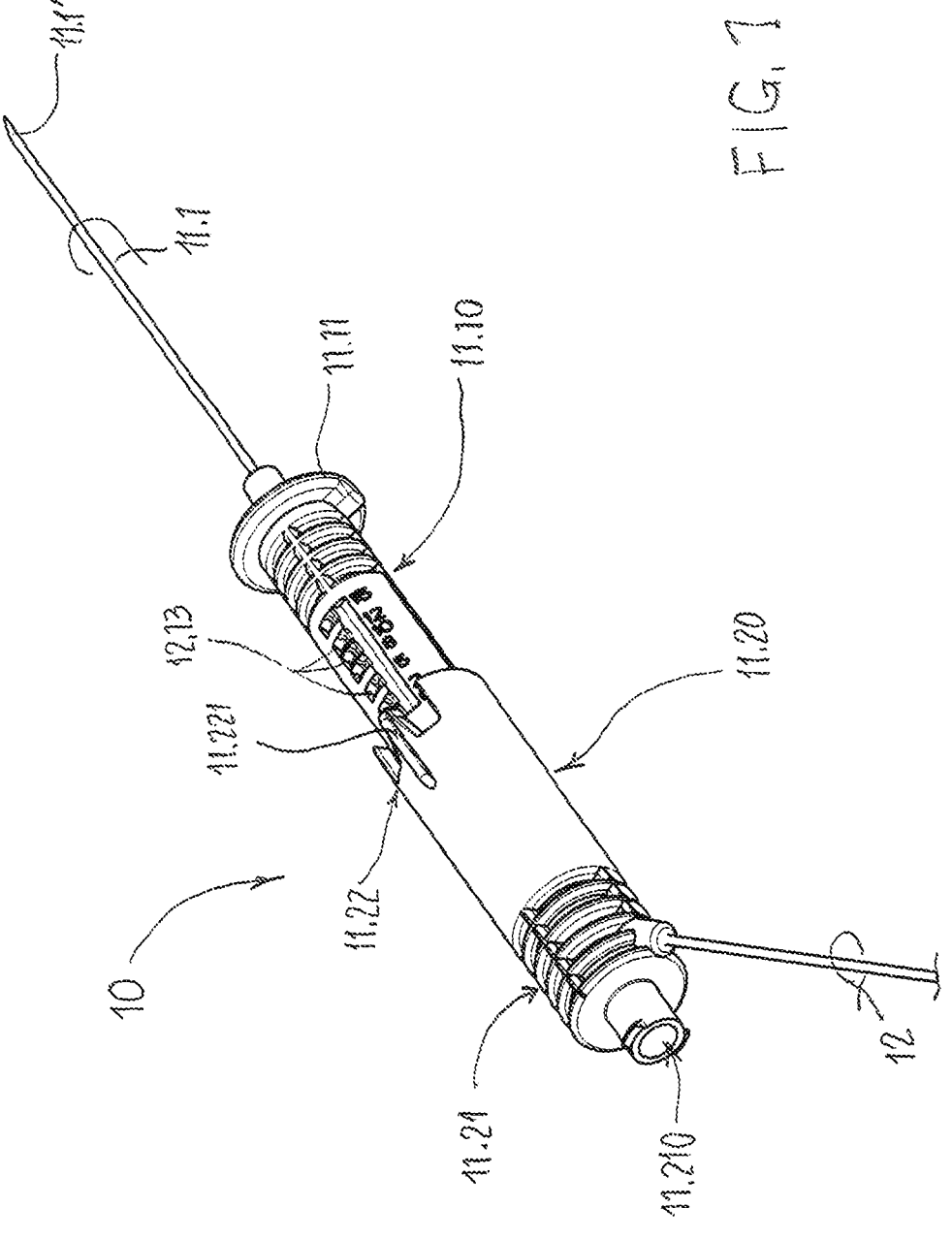
Figure 2:
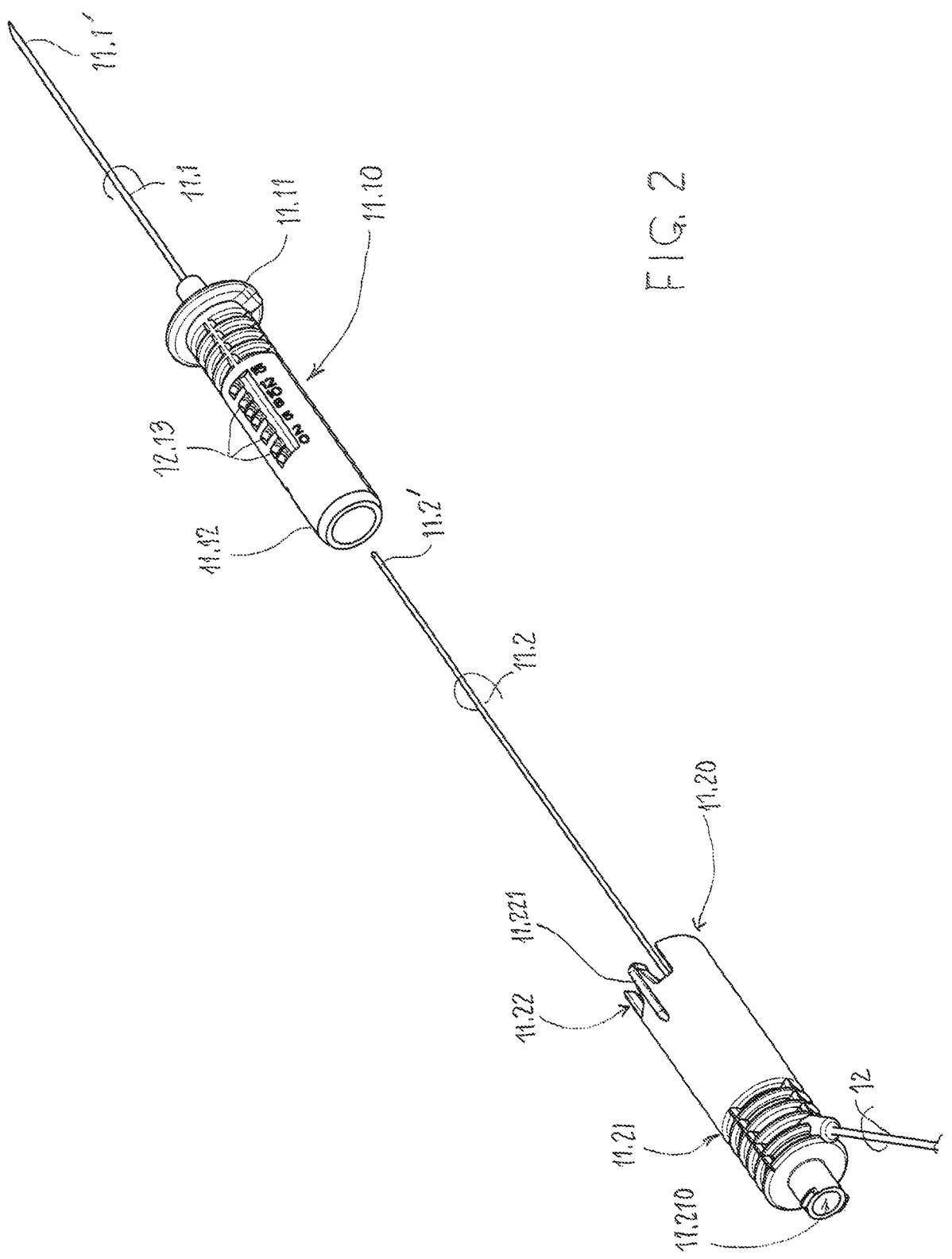
FIG. 2 is a view similar to that of FIG. 1, but in which the device is illustrated in exploded view, in which the cannula needle with its support is separate from the counter-cannula needle with its support.
Figures 9, 10:
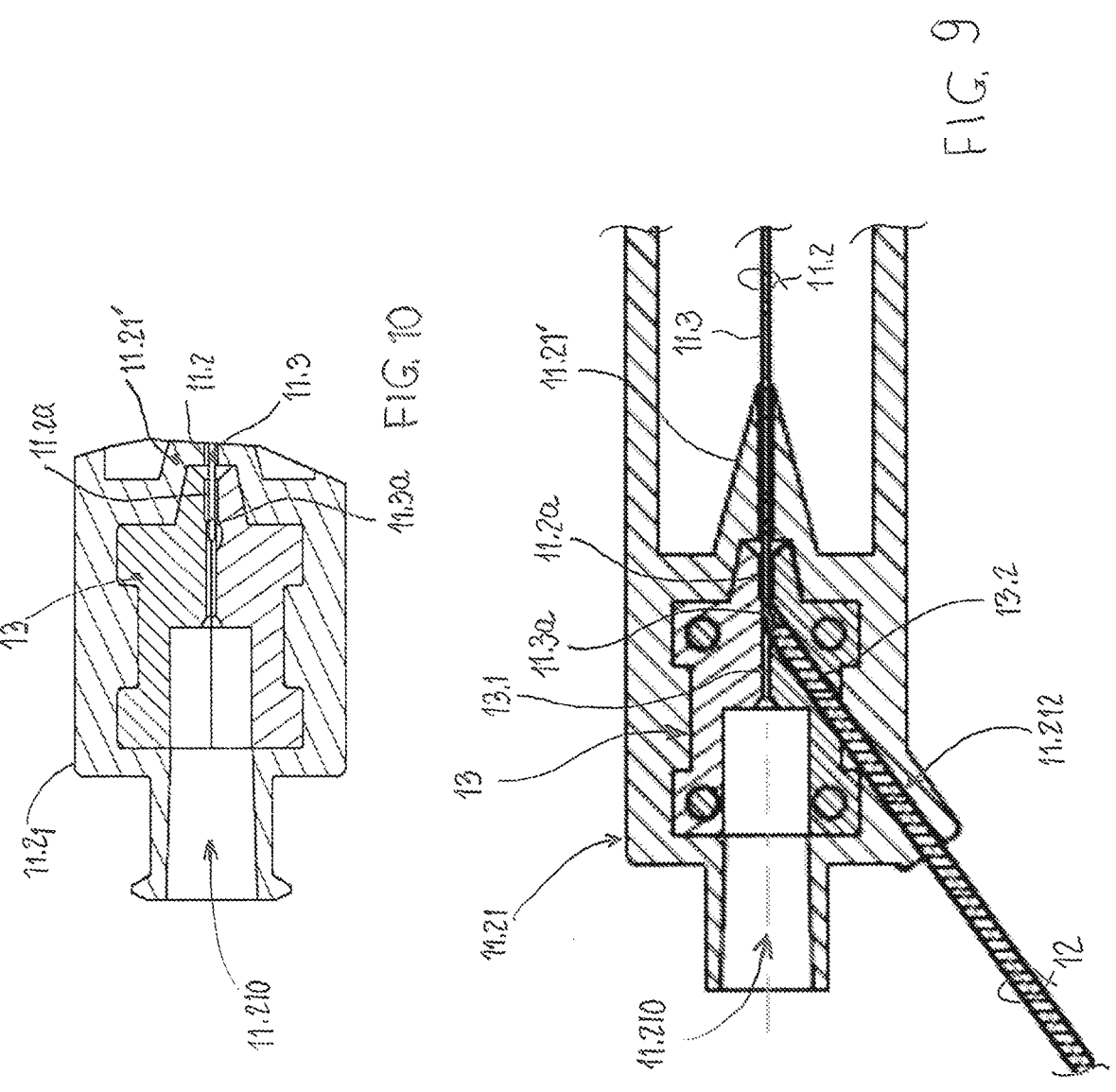
FIG. 9 is a detail view, on a larger scale, of detail IX of FIG. 7.
FIG. 10 is a detail view, on a larger scale, of detail X of FIG. 8.
Figure 16:
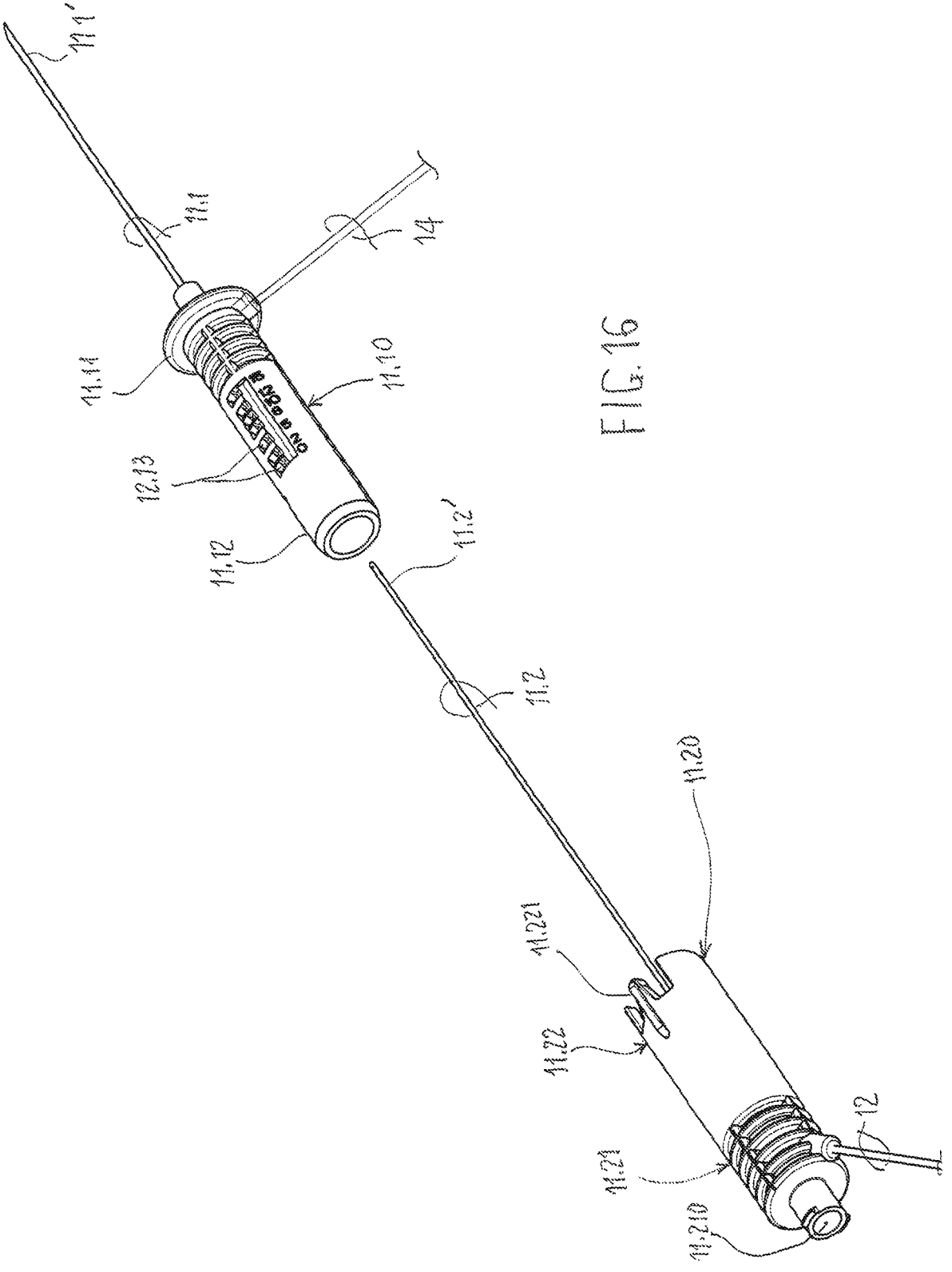

FIG. 15 is a detail view, on a larger scale, of detail XV of FIG. 14;

FIG. 16 is a perspective view of the electrostimulation device with double percutaneous coaxial needle, in the bipolar version, according to a second exemplary embodiment of the invention.

With reference to the drawing, 10 denotes the electrostimulation device with a double percutaneous coaxial needle, according to an embodiment of the present invention.

Said device 10 comprises:

two tubular bodies 11.10, 11.20, in plastic material, hereinafter referred to respectively as cannula support 11.10 and counter-cannula support 11.20, wherein the cannula support 11.10 and the counter-cannula support 11.20 are telescopically connected with the possibility of relative axial sliding, the cannula support 11.10 being partially included within the counter-cannula support 11.20;

a cannula needle 11.1 and a counter-cannula needle 11.2, hereinafter referred to respectively as cannula 11.1 and counter-cannula 11.2, axially perforated, in electrical conductive material, wherein the cannula 11.1 is supported fixed and coaxial with respect to the cannula support 11.10 and the counter-cannula 11.2 is supported fixed and coaxial with respect to the counter-cannula support 11.20 and wherein the counter-cannula 11.2 is inserted in a coaxial arrangement and is electrically insulated with respect to the cannula 11.1, with the possibility of relative axial sliding.

The cannula support 11.10 is configured, at a first axial end zone 11.11, so-called front end, as a bottom having an axial through hole, with respect to which an axial end of said cannula is fixed 11.1, the remainder of the cannula 11.1 extending beyond said front end 11.11 and towards the outside of the cannula support 11.10.

The cannula 11.1 has a sharp tip 11.1', distal with respect to said front end 11.11 of the cannula support 11.10 and suitable for skin puncture.

The counter-cannula support 11.20 comprises an integral internal diaphragm 11.21' provided in proximity to a first axial end zone 11.21, so-called rear end, distal with respect to said front end 11.11 of the cannula support 11.10.

Said integral internal diaphragm 11.21' comprises a through axial hole and defines in said counter-cannula support 11.20:

a first axial cavity 11.210, so-called rear cavity, open towards the outside at said rear end 11.21, wherein said rear cavity 11.210 has one internal side wall contiguous to said diaphragm 11.21', a second axial cavity 11.211, so-called front cavity, open towards the outside at a second axial end zone 11.22 of said counter-cannula support 11.20, axially opposite to said rear end 11.21, wherein said cannula support 11.10 is inserted into said front cavity 11.211, by means of a second axial end zone 11.12 of said cannula support 11.10, axially opposite to said front end 11.11, with the possibility of relative axial sliding together with the respective cannula 11.1.

It is highlighted that the counter-cannula 11.2:

is fixed, in a coaxial arrangement, and with an intermediate portion, with respect to the axial hole of said internal diaphragm 11.21' of the counter-cannula support 11.20;

extends into and beyond said front cavity 11.211 of said counter-cannula support 11.20;

has a non-sharp tip 11.2', at a distal end with respect to said diaphragm 11.21' of the counter-cannula support 11.20, arranged beyond said counter-cannula support 11.20 and configured to extend outwards and inwards with respect to the sharp tip 11.1' of the cannula 11.1; has an axial end 11.2a, proximal to said diaphragm 11.21' opposite said non-sharp tip 11.2', extending beyond said diaphragm 11.21' in said rear cavity 11.210.

Furthermore, said device 10 comprises a mounting body 13 of said counter-cannula 11.2 with respect to said counter-cannula support 11.20, which is fixed in said rear cavity 11.210 of the counter-cannula support 11.20 and has at least one outer side wall facing towards and contiguous with respect to said inner side wall of said rear cavity 11.210 of said counter-cannula support 11.20.

It is highlighted that said mounting body 13 is made of electrically insulating material, for example in plastic material, includes a first hole 13.1, which is axially aligned with said axial hole of the diaphragm 11.21' of the counter-cannula support 11.20, and comprises a second through hole 13.2, lateral with respect to said first hole 13.1 and extending between said first hole 13.1, on which the hole 13.2 is open, and said at least one outer side wall of said mounting body 13, on which the hole 13.2 itself is open. The counter-cannula 11.2 has said axial end 11.2a sealingly inserted in said first hole 13.1 of said mounting body 13 and comprises a thermocouple means 11.3, fixed and coaxially arranged therein. Said thermocouple means 11.3 has a first electrically conductive axial end 11.3a, arranged outside the axial end 11.2a of the counter-cannula 11.2 and inside said first hole 13.1 of the mounting body 13.

A first flexible insulated electric conductor 12 has an intermediate portion inserted in said second through hole 13.2 of the mounting body 13 and a first electrically conductive end electrically connected with respect to a said first end 11.3a of said thermocouple means 11.3, while a second end of said thermocouple means 11.3, axially opposed to said first end 11.3a, is arranged at said non-sharp tip 11.2' of the counter-cannula 11.2 and is fixed to said non-sharp tip 11.2' of said counter-cannula 11.2.

Said counter-cannula support 11.20 comprises, in said rear end 11.21, a through hole 11.212, whose axis is axially aligned with the axis of said second hole 13.2 of said mounting body 13. Said first insulated electrical conductor 12 has a further portion inserted in said through hole 11.212 of the counter-cannula support 11.20 and is branched outside the counter-cannula support 11.20. Said first insulated electrical conductor 12 is electrically connected, by means of a second electrically conductive end, with respect to an external electrical control circuit (which is known and not explained). By means of the aforesaid arrangement, said counter-cannula 11.2 is configured as U.T.A. ("Uncoring Tip Advance") Electrode Probe, whose primary function is to adjust the active tip of the device 10, suitable for the procedure, and also to make the cannula 11.1 of the non-coring type. The U.T.A. Electrode Probe itself comprises said thermocouple means 11.3 suitable for monitoring and detecting the electrical functions of the electrical control circuit and for the correct operation of the procedure, in relation to the basic parameters set by a doctor using an electrical pulse generator device (per se known and not illustrated), so-called "auxiliary RF generator", included in said external electric control circuit.

For example, in a monopolar configuration of the device 10, as illustrated hereabove, said external electric control circuit may comprise said electric pulse generator and a neutral dispersion plate, adapted to close the electric circuit between a negative pole and a positive pole. It is enhanced that, in this arrangement, the cannula 11.1 is electrically insulated over its entire outer surface, for example by means of an electrically insulating coating.

On the other hand, according to another embodiment illustrated in FIG. 18, in a bipolar configuration of the device 10, said insulated electric conductor 12 is electrically connected in a suitable external electric circuit, with respect to which also said cannula 11.1 is electrically connected by means of a first conductive end of a second flexible insulated electric conductor 14, which is electrically connected, by means of a second conductive end, at the end of said cannula 11.1 fixed with respect to said bottom in the first end zone 11.11 of the cannula support 11.10. It should be noted that, in this arrangement, the cannula 11.1 has at least one electrically conductive end portion, while it is electrically insulated, for example by means of an electrically insulating coating, over the entire remaining part of its outer surface.

By means of the aforementioned arrangement, cannula 11.1 and counter-cannula 11.2, coupled each other with the possibility of relative axial sliding, provide a transcutaneous needle means with an indifferent tip and variable in length, which can be stimulated and thermodamaging through an active tip 11.1', 11.2' disposed in the distal part with respect to said first end zone 11.11 of the cannula support 11.10.

It is enhanced that said mounting body 13 comprises two half-bodies 13.3, juxtaposed and mating at respective opposite faces in a plane containing the axes of said first hole 13.1 and said second hole 13.2 of the mounting body 13.

In particular, each of said opposite faces of the half-bodies 13.3 has a respective first channel and a respective second channel, wherein said first channel is extended over the entire length of the assembled body 13 and said second channel extends laterally and communicates with respect to said first channel. By means of this arrangement said two juxtaposed and mutually fixed half-bodies 13.3 provide, by means of said respective first channel and second channel, reciprocally superimposed, said first hole 13.1 and said second hole 13.2 of the mounting body 13.

Furthermore, said opposite faces of said two half-bodies 13.3 have respective recesses 13.41 and mounting pins 13.42, mutually complementary and opposite, which form the assembly of the mounting body 13 by means of positive and/or force coupling. By means of this arrangement, the two half-bodies 13.3 can be assembled for example by hand, to form the mounting body 13, in which said end 11.2a of the counter-cannula 11.2 is inserted in the first hole 13.1 and said portion of the first insulated electric conductor 12 in the second hole 13.2.

On the other hand, it is highlighted that said cannula support 11.10 has, on the outer side surface and near said second end zone 11.12, a linear arrangement of recesses 12.13, extending in the axial direction and configured as notches of a graduated scale. Said counter-cannula support 11.20 comprises an integral elastic finger 11.221, projecting with respect to said second end zone 11.22 of the counter-cannula support 11.20. Said finger 11.221 has an elastically flexible tip, configured for cooperating in an elastic snap with each recess of said arrangement of recesses 12.13 provided in said side surface of said cannula support 11.10.

This arrangement makes it possible to set up in the device 10 a plurality of positions of stable telescopic extension or retraction of the cannula support 11.10 with respect to the counter-cannula support 11.20, in which the cannula 11.1 and the counter-cannula 11.2 assume different predetermined relative and operative positions. To each relative position of the counter-cannula 11.2 with respect to the cannula 11.1 corresponds a respective recess of said arrangement of recesses 12.13 of the cannula support 10, in which said elastic finger 11.221 of the counter-cannula support 11.20 can be engaged (and from which it can be disengaged), as a result of manual action by an operator.

It is to be noted that the rear end of the counter-cannula support 11.20 is configured for sealing connection with liquid infusion devices, which are delivered through the counter-cannula 11.2. In particular, it should be noted that the counter-cannula support 11.20 comprises, in correspondence with said first axial end zone 11.21, a "luer lock" type connection communicating with said rear cavity 11.210 for the intrinsic infusion of liquids through the counter-cannula 11.2.

The present invention also provides a process for manufacturing an electrostimulation device 10 with double coaxial percutaneous needle, wherein said device 10 comprises:

> two tubular bodies 11.10, 11.20, in plastic material, hereinafter referred to respectively as cannula support 11.10 and counter-cannula support 11.20, wherein the cannula support 11.10 and the counter-cannula support 11.20 are telescopically connected with the possibility of relative axial sliding, the cannula support 11.10 being partially inserted in said counter-cannula support 11.20;
> a cannula needle 11.1 and a counter-cannula needle 11.2, hereinafter referred to respectively as cannula 11.1 and counter-cannula 11.2, axially perforated, in electrical conductive material, wherein the cannula 11.1 is supported fixed and coaxial with respect to the cannula support 11.10 and the counter-cannula 11.2 is supported fixed and coaxial with respect to the counter-cannula support 11.20 and wherein the counter-cannula 11.2 is inserted in a coaxial arrangement and is electrically insulated with respect to the cannula 11.1, with the possibility of relative axial sliding.

According to the present invention the aforementioned process is characterized in that it comprises the following production steps of said counter-cannula support 11.20 with relative counter-cannula 11.2 fixed with respect to said counter-cannula support 11.20:

> providing a counter-cannula 11.2, which has a first axial end 11.2a opposite a second axial end, so-called non-sharp tip 11.2';
> providing a thermocouple means 11.3, configured to be inserted and fixed in said counter-cannula 11.2 in an axial arrangement and having a first axial end 11.31, electrically conductive, and a second axial end opposite to said first end 11.31;
> inserting and fixing said thermocouple means 11.3 in an axial arrangement in said counter-cannula 11.2, placing said first axial end 11.31 of said thermocouple means 11.3 in proximity to said first axial end 11.2a of the counter-cannula 11.2 and said second axial end of said thermocouple means 11.3 in proximity to said non-sharp tip;
> providing a first insulated electrical conductor 12, hereinafter referred to as the first conductor 12, which has a first electrically conductive end and a second electrically conductive end;
> making a mounting body 13 of said counter-cannula 11.2 with respect to said counter-cannula support 11.20, wherein said mounting body 13 is made of electrically insulating material and is provided with:
> at least one outer side wall;

> a first hole 13.1, configured to house a first part, the so-called end part, of said axial end 11.2a of the counter-cannula 11.2,
> a second hole 13.2, passing through and extending between said first hole 13.1 and said at least one outer side wall of said mounting body 13, wherein said second hole 13.2 is configured to house a first section of a first part of said first conductor 12, wherein said first section is contiguous to said first electrically conductive end of said first conductor 12, which is arranged outside said second hole 13.2;
> inserting said end part of said axial end 11.2a of the counter-cannula 11.2 in said first hole 13.1 of said mounting body 13, inserting said first section of said first part of said first conductor 12 in said second hole 13.2 of said mounting body 13 and juxtaposing said first electrically conductive end of said first conductor 12 and said first axial end 11.31 of said thermocouple means 11.3, making a fixed electrical contact;
> providing a mould configured for injection moulding of molten plastic material and metal and providing in said mould moulding means for said counter-cannula support 11.20, wherein said moulding means are configured as injection cavities of molten plastic material;
> arranging in said injection cavity of molten plastic material said mounting body 13 including said end part of said axial end 11.2a of said counter-cannula 11.2, said first section of said first part of said first conductor 12 and said fixed electrical contact between said first electrically conductive end of said first conductor 12 and said first axial end 11.31 of said thermocouple means 13;
> configuring said injection cavity of molten plastic material to form said counter-cannula support 11.20 as a tubular body and to form in said counter-cannula support 11.20:
> > an integral internal diaphragm 11.21', which:
> > > includes a through axial hole, and
> > > defines, in said counter-cannula support 11.20, a first axial cavity 11.210, so-called rear cavity, having at least one inner side wall contiguous to said diaphragm 11.21', at a first axial end zone 11.21, and a second axial cavity 11.211, so-called front cavity, open towards the outside at a second axial end zone 11.22, opposite to said first axial end zone 11.21, of the counter-cannula support 11.20, and
> > a through hole 11.212, which:
> > > is made at said rear end 11.21, and
> > > has the axis aligned with the axis of said second hole 13.2 of said mounting body 13 and is configured to contain a second section of said first part of said first conductor 12 distal to said first electrically conductive end;
> branching said first conductor 12 outside said injection cavity of molten plastic material of said mould and outside said mould, by means of said second part of said first conductor 12 having said second electrically conductive end;
> closing said mould and carrying out the injection of molten plastic material into said injection cavity of molten plastic material of said mould, burying in the injected molten plastic material:
> > said mounting body 13 including, at said first axial cavity 11.210 of said counter-cannula support 11.20, said end part of said axial end 11.2a of said counter-cannula 11.2, said first section of said first part of said first conductor 12 and said fixed electrical contact between said first electrically conductive end of said first conductor 12 and said first axial end 11.31 of said thermocouple means 13;

said second section of said first part of the first conductor 12;

a further part of said axial end 11.2*a* of said counter-cannula 11.2 contiguous to said end part of said counter-cannula and sealed in said axial through hole of said diaphragm 11.21' of said counter-cannula support 11.20;

causing the injected molten plastic material to harden and extracting said counter-cannula support 11.20 from said mould, wherein said mounting body 13, said axial end 11.2*a* of said counter-cannula 11.2 and said second section of said first part of the first conductor 12 are incorporated.

Furthermore, the process according to the invention is characterized by the step consisting in forming said mounting body 13 into two separate half-bodies 13.3, which are then juxtaposed and made to mate by means of respective opposite faces at a plane containing the axes of said first hole 13.1 and of said second hole 13.2 of the mounting body 13.

The process according to the invention is further characterized by the step consisting in providing said opposite faces of said two half-bodies 13.3 with respective recesses and corresponding mounting pins, which are made to cooperate to carry out the assembly of the mounting body 13 by positive and/or force coupling.

Also, the process according to the invention is characterized by the steps consisting in providing in each of said opposite faces of the half-bodies 13.1 a respective first channel and a respective second channel, in which said first channel extends over the entire length of the assembled body 13 and said second channel extends laterally and communicates with respect to said first channel, and in juxtaposing said two half-bodies 13.3 forming said first hole 13.1 and said second hole 13.2 of the mounting body 13 by overlapping the respective first and second channels.

It is also to be noted that the process according to the invention is characterized by the step consisting in forming, on an outer side surface of an end portion 11.12 of said cannula support 11.1, a linear arrangement of recesses 12.13, extended in axial direction and configured as notches of a graduated scale, and in forming in said counter-cannula support 11.20 an elastic finger 11.221, projecting with respect to said second end zone 11.22 of the counter-cannula support 11.20 and having an elastically flexible tip, configured for cooperating in an elastic snap with each recess of said arrangement of recesses 12.13 formed in said outer side surface of said cannula support 11.10.

As can be seen from the foregoing, the present invention achieves the objects set forth in the initial part of the present description in a simple and effective way.

The invention claimed is:

1. An electrostimulation device with a double percutaneous coaxial needle, comprising:

two tubular bodies, in plastic material, hereinafter referred to respectively as cannula support and counter-cannula support, wherein the cannula support and the counter-cannula support; are telescopically connected with the possibility of relative axial sliding;

a cannula needle and a counter-cannula needle, hereinafter referred to respectively as cannula and counter-cannula, axially perforated, in electrical conductive material, wherein the cannula is supported fixed and coaxial with respect to the cannula support and the counter-cannula is supported fixed and coaxial with respect to the counter-cannula support and wherein the counter-cannula is inserted in a coaxial arrangement and is electrically insulated with respect to the cannula, with the possibility of relative axial sliding; wherein the cannula support is, at least partially, included within the counter-cannula support with the possibility of relative axial sliding.

2. The device according to claim 1, wherein:

the cannula support is configured, at a first axial end zone, so-called front end, as a bottom having an axial through hole, with respect to which an axial end of said cannula is fixed, the remainder of the cannula extending beyond said front end and towards the outside of the cannula support;

the cannula has a sharp tip, distal with respect to said front end of the cannula support and suitable for skin puncture;

the counter-cannula support comprises an integral internal diaphragm provided in proximity to a first axial end zone, so-called rear end, distal with respect to said front end of the cannula support, wherein said internal diaphragm:

comprises a through axial hole and defines in said counter-cannula support:

a first axial cavity, so-called rear cavity, open towards the outside at said rear end, wherein said rear cavity has at least one internal side wall contiguous to said diaphragm, and a second axial cavity, so-called front cavity, open towards the outside at a second axial end zone of said counter-cannula support, axially opposite to said rear end, wherein said cannula support is inserted into said front cavity, by means of a second axial end zone of said cannula support, axially opposite to said front end, with the possibility of relative axial sliding together with the respective cannula;

the counter-cannula:

is fixed, in a coaxial arrangement, and with an intermediate portion, with respect to the axial hole of said internal diaphragm of the counter-cannula support;

extends into and beyond said front cavity of said counter-cannula support;

has a non-sharp tip, at a distal end with respect to said diaphragm of the counter-cannula support, arranged beyond said counter-cannula support and configured to extend outwards and inwards with respect to the sharp tip of the cannula;

has an axial end, proximal to said diaphragm opposite said non-sharp tip, extending beyond said diaphragm in said rear cavity;

and in that it comprises:

a mounting body of said counter-cannula with respect to said counter-cannula support, which is fixed in said rear cavity of the counter-cannula support and has at least one outer side wall facing towards and contiguous with respect to said at least one inner side wall of said rear cavity of said counter-cannula support and wherein said mounting body:

is made of electrically insulating material, includes a first hole, which is axially aligned with said axial hole of the diaphragm of the counter-cannula support, and comprises a second through hole, lateral with respect to said first hole and extending between said first hole, on which the hole is open, and said at least one outer side wall of said mounting body, on which the hole itself is open;

wherein the counter-cannula has said axial end sealingly inserted in said first hole of said mounting body;

wherein a thermocouple means is inserted and fixed in said counter-cannula in an axial arrangement and has:

a first electrically conductive axial end, arranged inside said first hole of the mounting body; and electrically connected with respect to a first electrically conductive end of a first insulated electric conductor;

a second end, axially opposite to said first end, arranged at said non-sharp tip of the counter-cannula;

wherein said first insulated electrical conductor has an intermediate portion, contiguous to said first electrically conductive end, inserted in said second through hole of the mounting body;

wherein said counter-cannula support comprises, in said rear end, a through hole, whose axis is axially aligned with the axis of said second hole of said mounting body;

wherein said first insulated electrical conductor has a further portion inserted in said through hole of the counter-cannula support, is branched outside the counter-cannula support and is electrically connected, by means of a second electrically conductive end, with respect to an external electrical control circuit.

3. The device according to claim 1, having a monopolar configuration, wherein said external electric control circuit comprises an electric pulse generator and a neutral dispersion plate, adapted to close the electric circuit between a negative pole and a positive pole, and wherein said cannula is electrically insulated over its entire outer surface.

4. The device according to claim 1, having a bipolar configuration, wherein said cannula H is electrically connected with respect to said external electrical control circuit by means of a second insulated electrical conductor, and wherein the cannula has at least an electrically conductive end portion, while it is electrically insulated over the entire remaining part of its outer surface.

5. The electrostimulation device according to claim 1, wherein said mounting body comprises two half-bodies, juxtaposed and mating at respective opposite faces in a plane containing the axes of said first hole and said second hole of the mounting body.

6. The electrostimulation device according to claim 5, wherein said opposite faces of said two half-bodies have respective recesses and mounting pins, mutually complementary and opposite, which form the assembly of the mounting body by means of positive and/or force coupling.

7. The electrostimulation device according to claim 5, wherein each of said opposite faces of the half-bodies has a respective first channel and a respective second channel, wherein said first channel is extended over the entire length of the assembled body and said second channel extends laterally and communicates with respect to said first channel, so that said two juxtaposed and mutually fixed half-bodies provide, by means of said respective first channel and second channel, reciprocally superimposed, said first hole and said second hole of the mounting body.

8. The electrostimulation device according to claim 1, wherein said cannula support has, on an outer side surface, a linear arrangement of recesses, extending in the axial direction and configured as notches of a graduated scale, and in that said counter-cannula support comprises an elastic finger, projecting with respect to said second end zone of the counter-cannula support and having an elastically flexible tip, configured for cooperating in an elastic snap with each recess of said arrangement of recesses, provided in said side surface of said cannula support.

9. A process for manufacturing the electrostimulation device with a double percutaneous coaxial needle according to claim 1, wherein said device comprises:

two tubular bodies, in plastic material, hereinafter referred to respectively as cannula support and counter-cannula support, wherein the cannula support and the counter-cannula support; are telescopically connected with the possibility of relative axial sliding;

a cannula needle and a counter-cannula needle, hereinafter referred to respectively as cannula and counter-cannula, axially perforated, in electrical conductive material, wherein the cannula is supported fixed and coaxial with respect to the cannula support and the counter-cannula is supported fixed and coaxial with respect to the counter-cannula support and wherein the counter-cannula is inserted in a coaxial arrangement and is electrically insulated with respect to the cannula, with the possibility of relative axial sliding; wherein the cannula support is movably inserted, at least partially, in the counter-cannula support with the possibility of relative axial sliding.

10. The process according to claim 9, wherein it comprises the following production steps for producing said counter-cannula support with relative counter-cannula fixed with respect to said counter-cannula support:

providing a counter-cannula, which has a first axial end opposite a second axial end, so-called non-sharp tip;

providing a thermocouple means, configured to be inserted and fixed in said counter-cannula in an axial arrangement and having a first axial end, electrically conductive, and a second axial end opposite to said first end;

inserting and fixing said thermocouple means in an axial arrangement in said counter-cannula, placing said first axial end of said thermocouple means in proximity to said first axial end of the counter-cannula and said second axial end of said thermocouple means in proximity to said non-sharp tip;

providing a first insulated electrical conductor, hereinafter referred to as the first conductor, which has a first electrically conductive end and a second electrically conductive end;

making a mounting body of said counter-cannula with respect to said counter-cannula support, wherein said mounting body is made of electrically insulating material and is provided with:

at least one outer side wall;

a first hole, configured to house a first part, the so-called end part, of said axial end of the counter-cannula, a second hole, passing through and extending between said first hole and said at least one outer side wall of said mounting body, wherein said second hole is configured to house a first section of a first part of said first conductor, wherein said first section is contiguous to said first electrically conductive end of said first conductor, which is arranged outside said second hole;

inserting said end part of said axial end of the counter-cannula in said first hole of said mounting body, inserting said first section of said first part of said first conductor in said second hole of said mounting body and juxtaposing said first electrically conductive end of said first conductor and said first axial end of said thermocouple means, making a fixed electrical contact;

providing a mould configured for injection moulding of molten plastic material and metal and providing in said mould moulding means for said counter-cannula support, wherein said moulding means are configured as injection cavities of molten plastic material;

arranging in said injection cavity of molten plastic material said mounting body including said end part of said axial end of said counter-cannula, said first section of said first part of said first conductor and said fixed electrical contact between said first electrically conductive end of said first conductor and said first axial end of said thermocouple means;

configuring said injection cavity of molten plastic material to form said counter-cannula support as a tubular body and to form in said counter-cannula support:

an integral internal diaphragm, which:

includes a through axial hole, and defines, in said counter-cannula support, a first axial cavity, so-called rear cavity, having at least one inner side wall contiguous to said diaphragm, at a first axial end zone, and a second axial cavity, so-called front cavity, open towards the outside at a second axial end zone, opposite to said first axial end zone, of the counter-cannula support, and a through hole, which:

is made at said rear end, and has the axis aligned with the axis of said second hole of said mounting body and is configured to contain a second section of said first part of said first conductor distal to said first electrically conductive end;

branching said first conductor outside said injection cavity of molten plastic material of said mould and outside said mould, by means of said second part of said first conductor having said second electrically conductive end;

closing said mould and carrying out the injection of molten plastic material into said injection cavity of molten plastic material of said mould, burying in the injected molten plastic material:

said mounting body including, at said first axial cavity of said counter-cannula support, said end part of said axial end of said counter-cannula, said first section of said first part of said first conductor and said fixed electrical contact between said first electrically conductive end of said first conductor and said first axial end of said thermocouple means;

said second section of said first part of the first conductor;

a further part of said axial end of said counter-cannula contiguous to said end part of said counter-cannula and sealed in said axial through hole of said diaphragm of said counter-cannula support;

causing the injected molten plastic material to harden and extracting said counter-cannula support from said mould, wherein said mounting body, said axial end of said counter-cannula and said second section of said first part of the first conductor are incorporated.

11. The process according to claim 10 for the production of a device, characterized by the step consisting in forming a mounting body into two separate half-bodies, which are then juxtaposed and made to mate by means of respective opposite faces at a plane containing axes of a first hole and of a second hole; of the mounting body.

12. The process according to claim 10 for the production of a device, characterized by the step consisting in providing opposite faces of two half-bodies with respective recesses and corresponding mounting pins, which are made to cooperate to carry out the assembly of a mounting body by positive and/or force coupling.

13. The process according to claim 10 for the production of a device wherein the steps consisting in providing in each opposite faces of half-bodies a respective first channel and a respective second channel, in which said first channel extends over the entire length of an assembled body and said second channel extends laterally and communicates with respect to said first channel, and in juxtaposing said two half-bodies forming a first hole and a second hole of a mounting body by overlapping the respective first and second channels.

14. The process according to claim 10 for the production of a device wherein the step consisting in forming, on an outer side surface of an end portion of a cannula support, a linear arrangement of recesses, extended in axial direction and configured as notches of a graduated scale, and in forming in a counter-cannula support an elastic finger, projecting with respect to a second end zone of the counter-cannula support and having an elastically flexible tip, configured for cooperating in an elastic snap with each recess of an arrangement of recesses formed in said outer side surface of said cannula support.

*    *    *    *    *